United States Patent [19]
Skinkle et al.

[11] Patent Number: 5,891,080
[45] Date of Patent: *Apr. 6, 1999

[54] BIOLOGICAL FLUID CASSETTE AND TUBING SET

[75] Inventors: David Skinkle, Evergreen; Timothy Igoe, Lakewood, both of Colo.; Lawrence Darnell, Cypress, Tex.

[73] Assignee: Cobe Laboratories, Inc., Lakewood, Colo.

[*] Notice: The term of this patent shall not extend beyond the expiration date of Pat. No. 5,584,320.

[21] Appl. No.: 450,537

[22] Filed: May 25, 1995

Related U.S. Application Data

[62] Division of Ser. No. 332,814, Oct. 31, 1994, Pat. No. 5,584,320.

[51] Int. Cl.⁶ ................................................. A61M 37/00
[52] U.S. Cl. .................................................................. 604/4
[58] Field of Search ............................................. 604/4–6

[56] References Cited

U.S. PATENT DOCUMENTS

| | | |
|---|---|---|
| 4,526,515 | 7/1985 | DeVries . |
| 4,585,436 | 4/1986 | Davis et al. ................................. 604/4 |
| 4,807,845 | 2/1989 | Darnell . |
| 4,865,584 | 9/1989 | Epstein et al. . |
| 5,273,517 | 12/1993 | Barone et al. . |
| 5,482,440 | 1/1996 | Dennehey et al. . |
| 5,584,320 | 12/1996 | Skinkle et al. .......................... 137/565 |

*Primary Examiner*—John G. Weiss
*Assistant Examiner*—Dennis Ruhl
*Attorney, Agent, or Firm*—Finnegan, Henderson, Farabow, Garrett, & Dunner, L.L.P.

[57] ABSTRACT

An apparatus for managing and controlling fluid flow through a plurality of fluid conduits includes a chassis, a plurality of conduit occluders mounted in the chassis, each occluder for association with at least one of the plurality of fluid conduits and each being selectively actuatable between an open position permitting fluid flow through a respective fluid conduit and a closed position obstructing conduit fluid flow. A single actuator is mounted in the chassis, the actuator for adjusting the plurality of occluders between the open and closed positions. A roller cage is also mounted in the chassis for mechanically interconnecting the actuator to the plurality of conduit occluders so that the single actuator is mechanically capable of maintaining one of the plurality occluders in the closed position while maintaining another of the plurality of occluders in the open position.

13 Claims, 6 Drawing Sheets

BIOLOGICAL FLUID CASSETTE AND TUBING SET

This is a division of application Ser. No. 08/332,814, filed Oct. 31, 1994 now U.S. Pat. No. 5,584,320.

BACKGROUND OF THE INVENTION

1. Field of the Invention

The invention relates to a device for controlling the flow of fluids through PVC tubing. The device has particular application in blood salvage units used to remove blood from a patient before or during surgery and clean the blood for reinfusion into the patient.

2. Description of the Related Art

Surgical patients often require blood infusion during surgical procedures to replace lost blood volume. Due to an increased risk of contracting communicable diseases such as AIDS from blood donors, it has become more desirable in recent years to replace lost blood volume with a patient's own blood. This can be accomplished in two ways. Prior to surgery, blood can be removed from a patient and stored for later use. Alternatively, blood may be suctioned from surgical cavities during a surgical procedure, cleaned, and reinfused into a patient during the same procedure.

In both instances, the blood must be processed before reinfusion. This processing includes centrifuging the blood to separate red blood cells from waste product and plasma, and rinsing the red blood cells. This process requires an iterative rinsing and centrifuging operation in order to insure that the red blood cells are completely clean.

During this process, biological and medical fluids are typically passed through numerous tubing lines connected to a blood cell separator unit. Tubing lines have to be opened and closed at precise times in order to ensure that the blood is properly processed and that fluids do not enter the wrong lines. Such occurrences could have catastrophic effects.

Unfortunately, such procedures are usually carried out under the pressure of an emergency room and/or surgical situation, and therefore there is not only a need to enable an operator to quickly initiate the blood collection process, but also to provide a device that minimizes the risk of error.

Typical blood salvage equipment includes a series of occluders for controlling the flow of fluids through the blood salvage unit. A typical occluder includes a plunger that presses against a flexible piece of plastic tubing to block flow through the tubing. When the plunger is released, fluid flow through the tubing resumes. In the typical blood salvage unit, each plunger is associated with a separate actuator whose operation is controlled by software. In the event of a software or electrical malfunction, two valves could open at the same time, with undesirable consequences.

As with most surgical procedures, time is of the essence and the time it takes to prepare a medical device for use can be critical. Some manufacturers therefore sell preassembled packages of centrifuge bowls, plastic tubing, and plastic fluid bags to minimize both connection errors and set-up time. However, even with these preassembled packages, an operator must still independently position a number of different tubes, which takes time and increases the risk of error.

SUMMARY OF THE INVENTION

Accordingly, the present invention is directed to an apparatus for managing and controlling fluid flow that substantially obviates one or more of the problems due to limitations and disadvantages of the related art.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

To achieve the objectives and in accordance with the purpose of the invention, as embodied and broadly described herein, the invention comprises an apparatus for managing and controlling fluid flow through a plurality of fluid conduits, the apparatus comprising a chassis; a plurality of conduit occluders mounted in the chassis, each occluder for association with at least one of the plurality of fluid conduits and each being selectively actuatable between an open position permitting fluid flow through a respective fluid conduit and a closed position obstructing conduit fluid flow; a single actuator mounted in the chassis, the actuator for adjusting the plurality of occluders between the open and closed positions; and means, mounted in the chassis, for mechanically interconnecting the actuator to the plurality of conduit occluders so the single actuator is mechanically capable of maintaining one of the plurality of occluders in the closed position while maintaining another of the plurality of occluders in the open position.

The invention also comprises a cassette for connection to first, second, and third tubes, and mountable on a chassis having a peristaltic pump and a series of plungers located thereon and a chassis protrusion protruding therefrom. The cassette comprises an approximately Y-shaped frame having a central leg portion, first and second arm portions, and a notched region between the first and second arm portions, the frame being mountable on the chassis so that the central leg lies adjacent the plungers and the chassis protrusion extends through the notched region. A main conduit is located on the frame and extends from the leg portion toward the first arm portion, the main conduit having a loop port in an area of the first arm portion. A first port is located in the frame for connecting the first tube to the main conduit, the first port for holding the first tube over a first plunger when the protrusion extends through the notched region. Second and third ports are also located in the frame for connecting the second and third tubes to the main conduit, the second and third ports for holding the second and third tubes over second and third plungers, respectively, when the protrusion extends through the notched region. A flexible tubing loop extends from the frame for engaging the peristaltic pump when the protrusion extends through the notched region, the tubing loop having a first end connected to the loop port and a second end secured to the second arm of the frame.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

Figure 1:
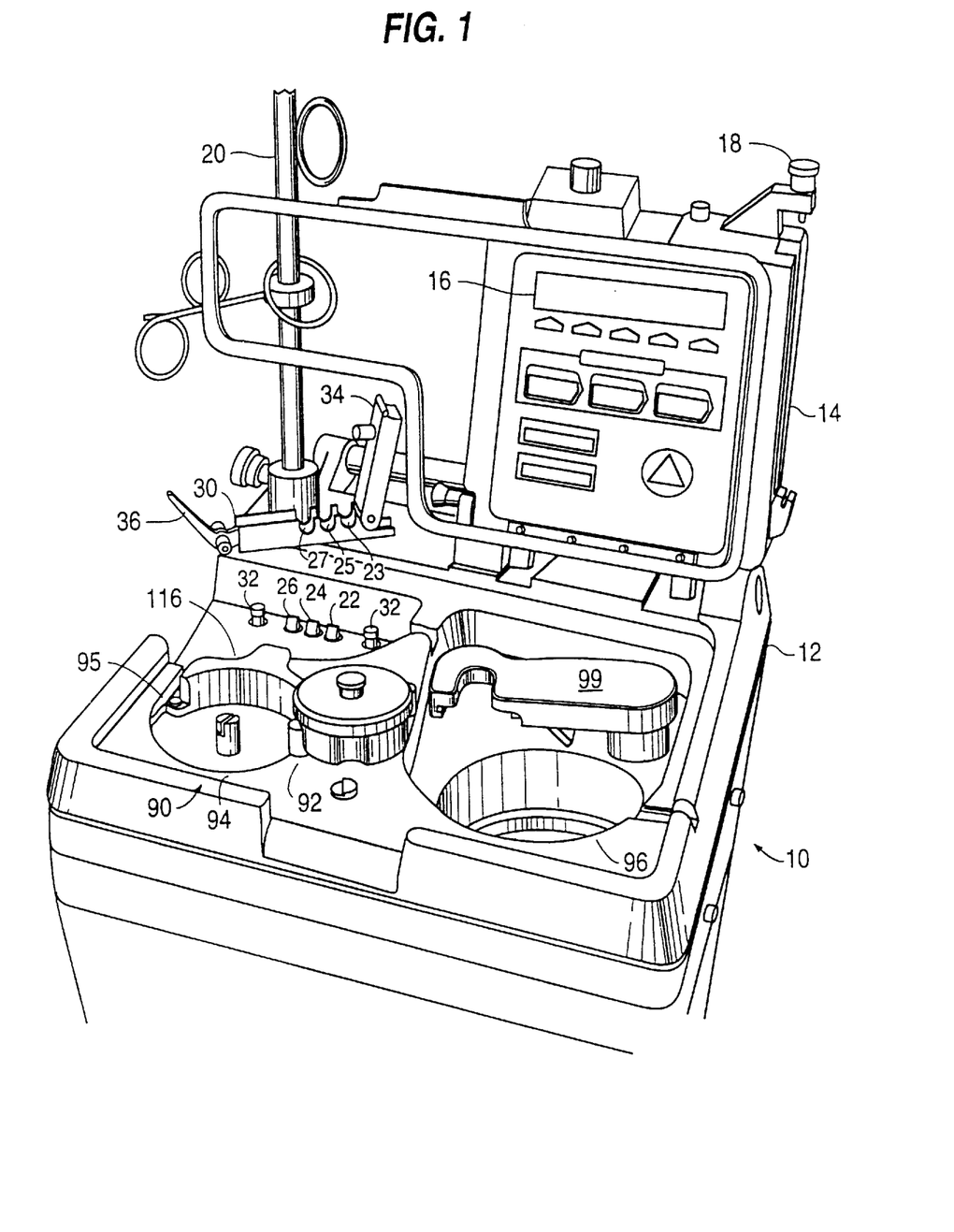
FIG. 1 is a perspective view of a blood salvaged apparatus in accordance with the invention.

In accordance with the invention there is provided an apparatus for managing and controlling fluid flow through a plurality of fluid conduits, the apparatus comprising a chassis. As embodied herein, and as illustrated in FIG. 1, an apparatus for managing and controlling fluid flow through a plurality of fluid conduits may include blood salvage apparatus 10 with chassis 12. The blood salvage apparatus 10 includes a control panel 14, with display device 16. A salvaged blood reservoir 150 (schematically illustrated in FIG. 7) may be connected to the side of the control panel with clamp 18, or may be supported by a bag pole 20. Preferably, salvaged blood reservoir 150 includes volume demarcations. Positioning of the salvaged blood reservoir 150 adjacent the control panel 14 enables an operator to readily ascertain the volume of blood salvaged. A detailed description of the blood reservoir is included in U.S. patent application Ser. No. 07/928,040, which is incorporated herein by reference.

Figure 7:
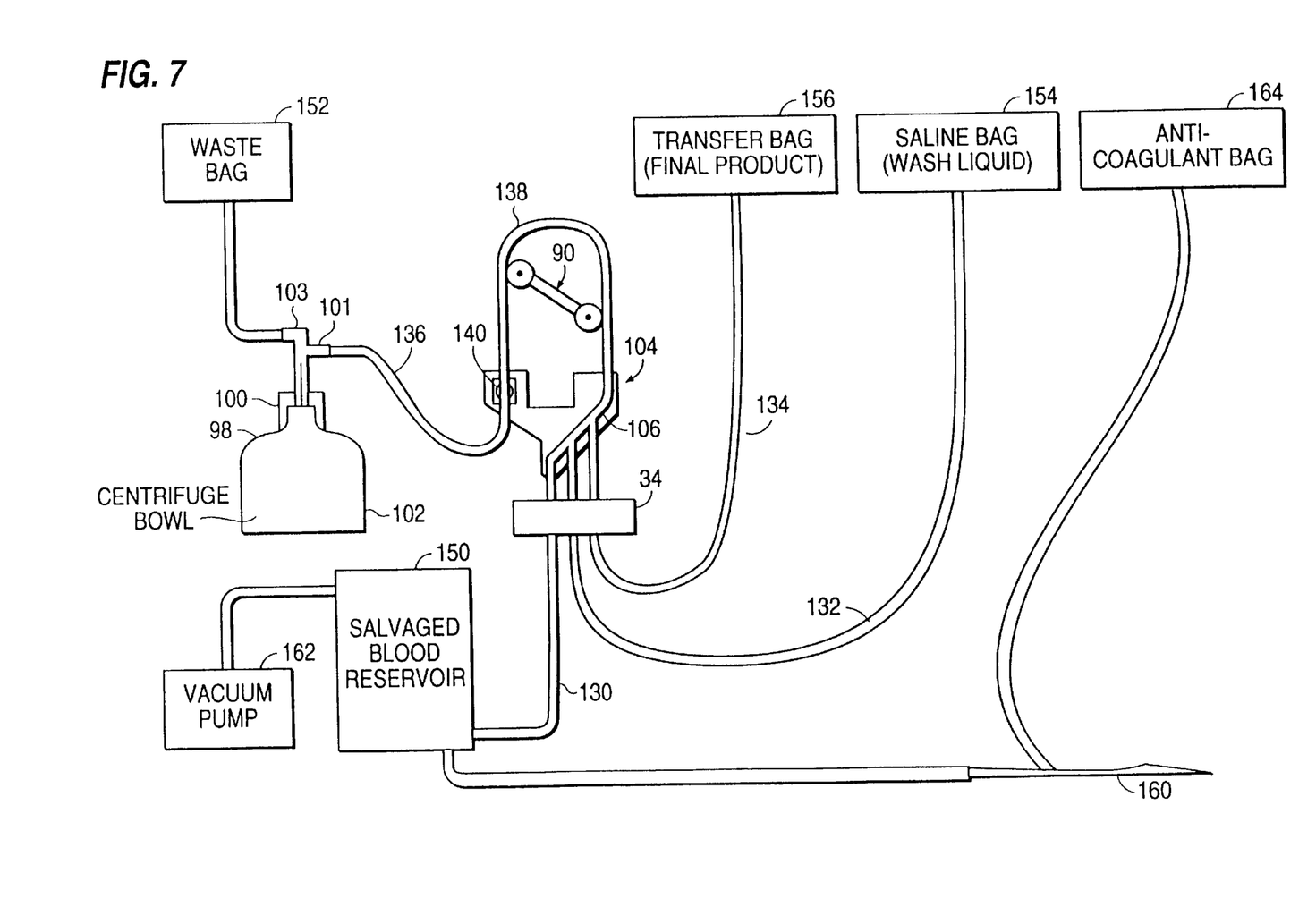
FIG. 7 is a schematic diagram illustrating the interconnection of the various components of the present invention.

Bag pole 20 is mounted to chassis 12 for supporting a saline bag 154 and a transfer bag 156, which are schematically illustrated in FIG. 7. A waste bag 152 may also be supported by bag pole 20, or can be attached to chassis 12. As will be discussed later in greater detail, waste bag 152, saline bag 154, transfer bag 156, and salvaged blood reservoir 150 are flow connected to centrifuge bowl 98 (schematically illustrated in FIG. 7) via fluid conduits, and fluid flow between these bags, blood reservoir 150, and centrifuge bowl 98 is controlled by blood salvage apparatus 10.

Figure 2:
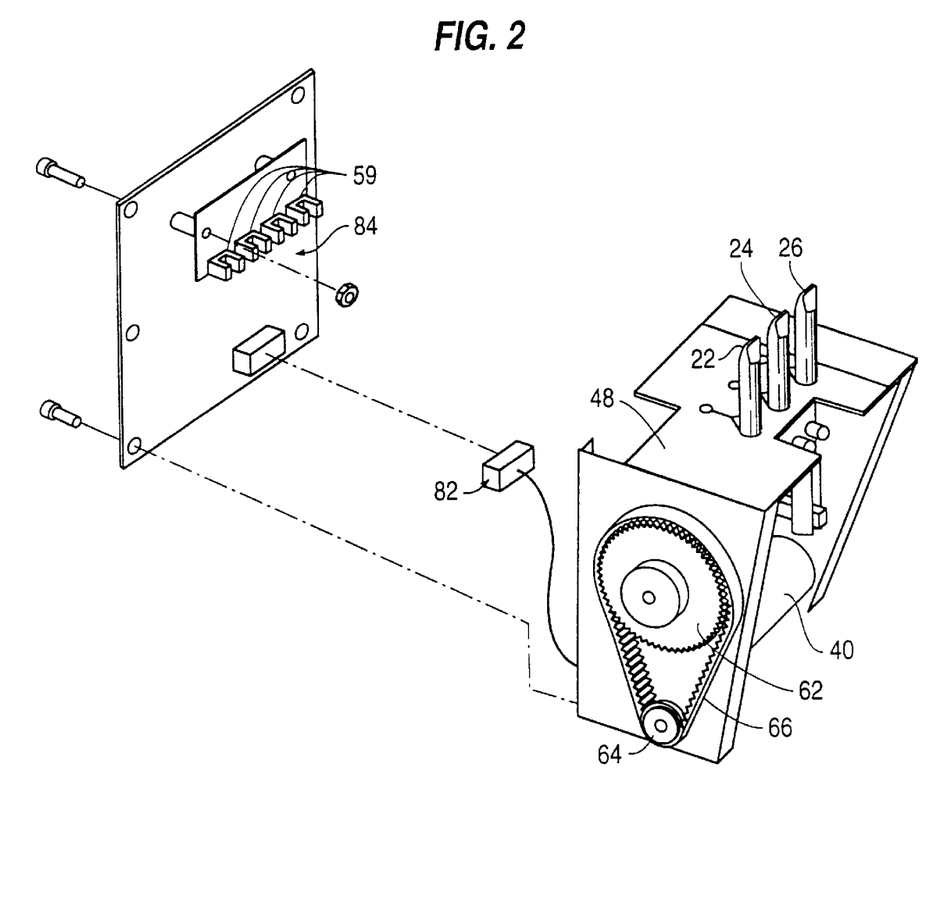
FIG. 2 is a partially exploded perspective view of an obturation assembly in accordance with the invention.
Figure 3:
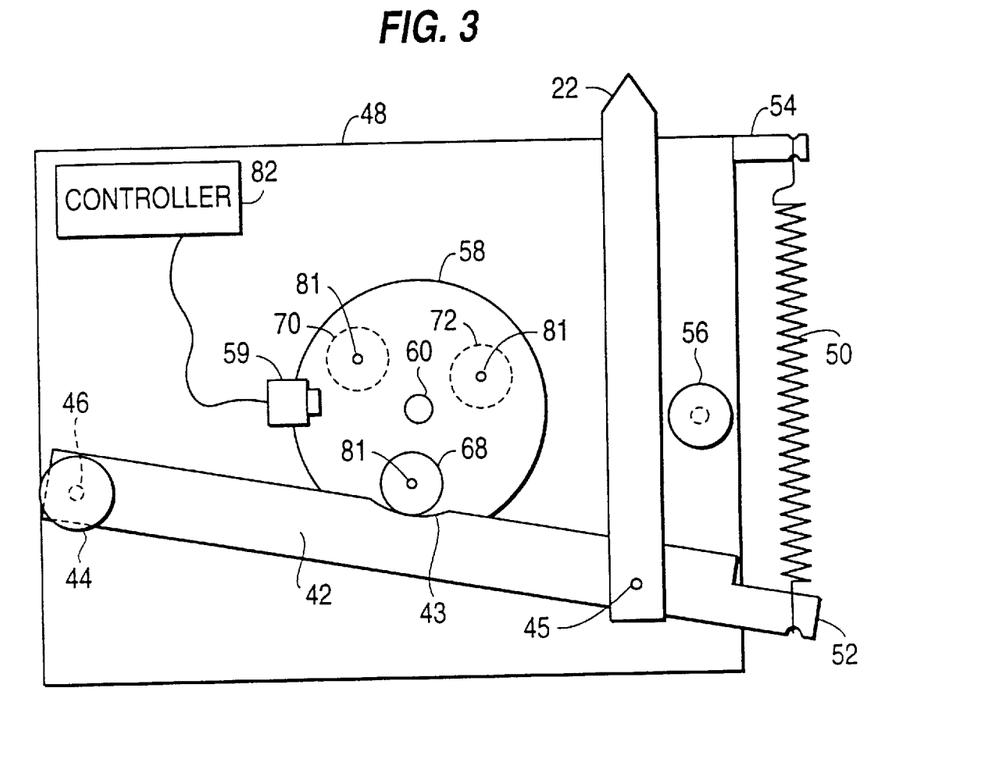
FIG. 3 is a schematic diagram of the obturation assembly of FIG. 2.

In accordance with the invention there is provided a plurality of conduit occluders mounted in the chassis, each occluder for association with at least one of the plurality of fluid conduits and each being selectively actuatable between an open position permitting fluid flow through a respective fluid conduit and a closed position obstructing conduit fluid flow. As embodied herein, and as illustrated in FIGS. 1–3, the conduit occluders may include polished stainless steel plungers 22, 24, and 26 each having an apexed occluding end. For ease of illustration, the apparatus is illustrated partially disassembled in FIG. 1 to illustrate the plungers 22, 24, 26. When fully assembled, a tube guide 30, having three channels 23, 25, and 27, engages posts 32 to guide and maintain segments of PVC tubing over each of the plungers. Once the tubing is in place, valve cap 34, which is pivotally connected to the tube guide 30, is pivoted to a closed position covering each tube, and is locked into place with cap lock 36.

Figure 4:
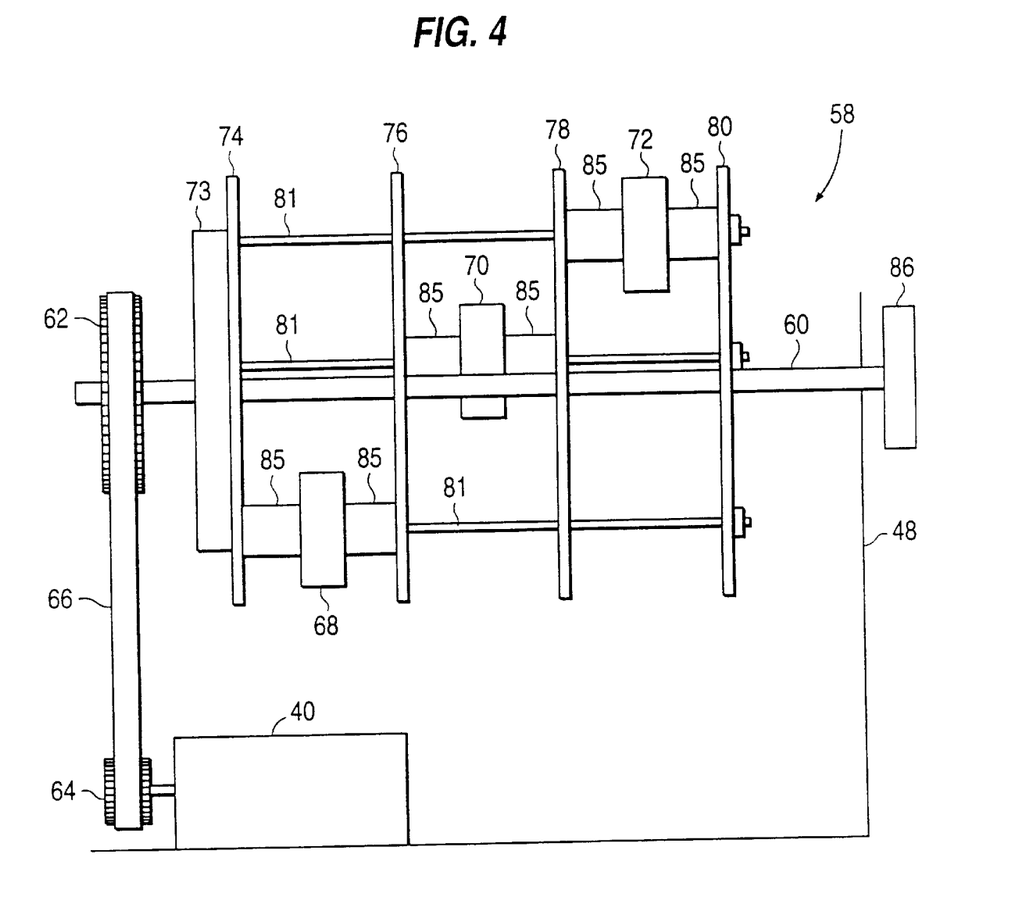
FIG. 4 is a front view of the roller cage assembly illustrated in FIG. 3.

Also in accordance with the present invention there is provided a single actuator mounted in the chassis, the actuator for adjusting the plurality of occluders between the open and closed positions. As embodied herein, and as best illustrated in FIGS. 2 and 4, the single actuator is an electric motor 40. Many types of electric motors are suitable for use. One example of a motor that has proved effective is a Bodine Hy-sync® AC 115 volt motor.

In accordance with the invention there is provided means, mounted in the chassis, for mechanically interconnecting the actuator to the plurality of conduit occluders so that the single actuator is mechanically capable of maintaining one of the plurality of occluders in the closed position while maintaining another of the plurality of occluders in the open position. As embodied herein, and as illustrated in FIG. 3, each plunger 22, 24, 26 is pivotally connected to an actuator beam 42 at pivot point 45, and each actuator beam 42 is in turn pivotally mounted to beam support 44 at pivot point 46. Beam support 44 in turn is mounted to occluder assembly frame 48. A spring 50 is interposed between the disconnected end 52 of actuator beam 42 and a spring pin 54 fixed to occluder assembly frame 48. Each spring 50 urges the apexed end of a respective plunger upward to an extended or closed position to deform and thereby obstruct flow in an associated fluid line. A stop bar 56, attached to frame 48, limits the upward movement of each actuator beam 42 to precisely define the closed position of each plunger. Although only one actuator beam/spring assembly is shown in FIG. 3, such an assembly is provided for each plunger 22, 24, 26.

As best illustrated in FIG. 4, a roller cage 58 is mounted on shaft 60, which is rotatably supported by occluder assembly frame 48. Shaft 60 also supports roller cage gear 62, which is coupled to motor gear 64 via toothed belt 66. Thus, rotation of motor gear 64 by motor 40 rotates roller cage 58.

As shown in FIGS. 3 and 4, roller cage 58 includes a series of rollers 68, 70, 72 rotatable on rods 81 attached to roller cage hub 73. Each of rollers 68, 70, and 72 is sandwiched between two of encoder disks 74, 76, 78, and 80, the encoder disks being coaxial with hub 73. Two spacers 85 are located on each rod 81, on either side of an associated roller. The spacers 85 fix the axial position of each roller so that each roller engages one of the actuator beams 42 to thereby move an associated plunger.

As shown in FIG. 3, each roller is mounted to a rod 81 in the roller cage angularly spaced 120° from each other roller. As a result, only one roller will engage a corresponding actuator beam at a time so that only one of the plungers is maintained in the open (retracted) position at a time. For example, when roller 68 is in the position shown in FIG. 4, it will engage actuator beam 42, as shown in FIG. 3, to thereby move the actuator beam and its associated plunger toward the open position against the force exerted by spring 50. To help maintain the plunger in the open position, actuator beam 42 may include a detent 43, as shown in FIG. 3, for receiving roller 68. At the same time, the other rollers 70 and 72 are disengaged from an associated actuator beam, and therefore the plungers associated with rollers 70 and 72 will be maintained in their closed positions.

Figure 5:
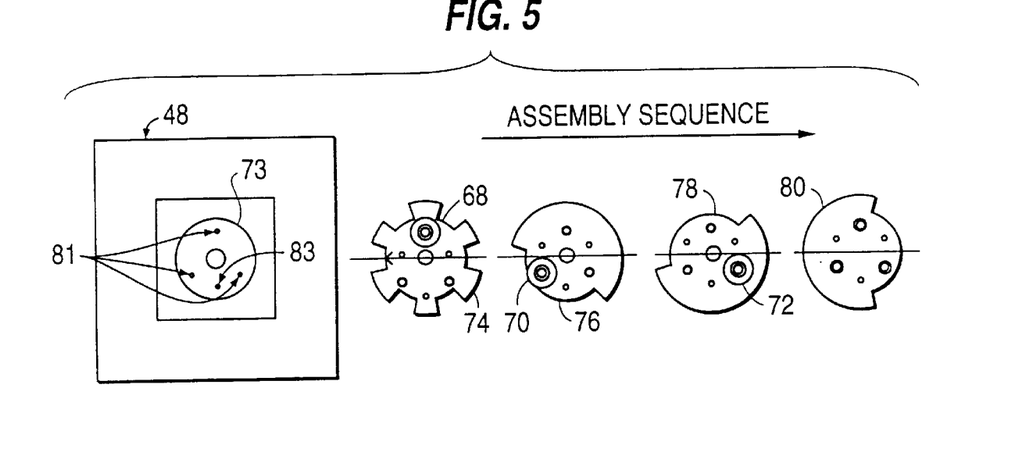
FIG. 5 is a side view of each of the encoder disks illustrated in FIG. 4.

The invention may also include means for sensing a rotational position of the roller cage and for generating a positional signal in accordance therewith. As embodied herein, and as illustrated in FIGS. 4 and 5, encoder disks 74, 76, 78, 80 may have a predetermined circumferential shape and/or cut-out regions (as shown in FIG. 5). Encoder disks 74, 76, 78, 80 are mounted on rods 81 and oriented with reference to locator pin 83 to ensure proper placement. The orientation of each encoder disk, determined with respect to its shape, is detected by a photodetector 59, which generates a positional signal that is sent to motor controller 82 mounted on circuit board 84, which is attached to occluder assembly frame 48 (see FIG. 2). Thus, the controller may activate the motor according to a programmed sequence or in response to manual manipulation of control panel 14 by an operator.

If, in the event of a power failure, motor 40 cannot be activated to rotate roller cage 58, there may be provided means for permitting an operator to manually rotate the roller cage to thereby manually position the plungers. As embodied herein, and as shown in FIG. 4, a handle 86 mounted to shaft 60 allows an operator to manually rotate shaft 60 to thereby rotate roller cage 58.

As shown in FIG. 1, a reversible peristaltic pump 90 is mounted in chassis 12. Rotor 92 of pump 90 is shown disassembled from rotatable shaft 94 in FIG. 1 for ease of illustration. Rotor 92 engages a loop segment 138 of main line 136 (shown in FIG. 7) to circulate fluid through the conduits in accordance with control signals sent by control panel 14.

Blood salvage apparatus 10 also includes a centrifuge 96 and a locking arm 99 mounted in chassis 12 as illustrated in FIG. 1. As schematically shown in FIG. 7, centrifuge 96 receives centrifuge bowl 98, which includes a stator 100 and rotor 102. Locking arm 99, which is pivotally attached to chassis 12, engages and locks stator 100 in place to prevent rotation of stator 100 when centrifuge 96 rotates rotor 102. Centrifuge bowls are known and can include several designs, one of which is disclosed in U.S. Pat. No. 5,141,486, which is incorporated herein by reference.

Figure 6:
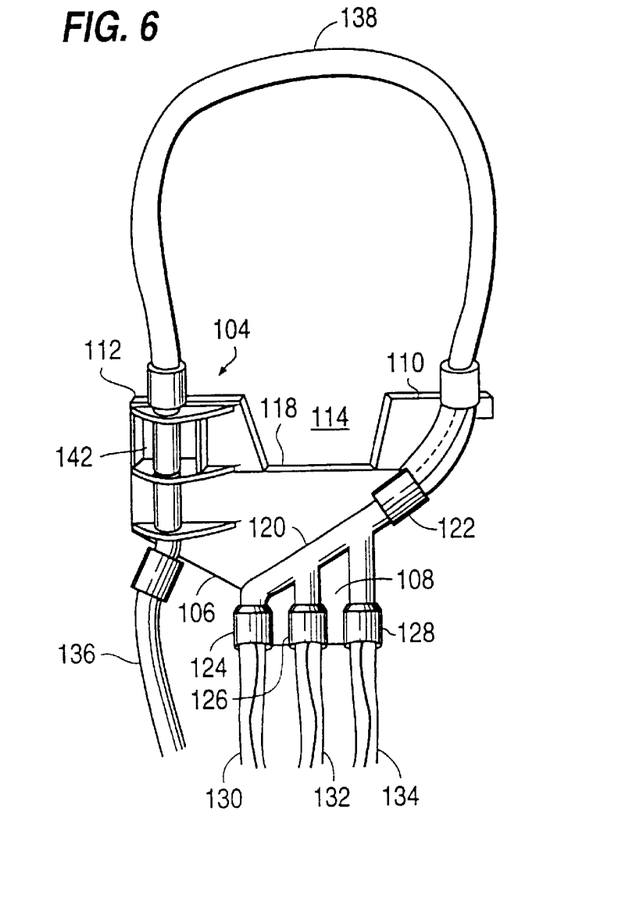
FIG. 6 is a top view of a fluid cassette in accordance with the present invention.

In practice, the fluid conduits must be accurately positioned over the appropriate plungers, and a portion 138 of main line 136 must be formed in a loop in order to engage the peristaltic pump 90. In addition, each of these tasks is often performed under the pressures and time restraints of an emergency room and/or surgical situation. Therefore, in order to facilitate alignment and attachment of the respective fluid conduits to the blood salvage apparatus 10 and in accordance with the invention, there is provided a cassette for connection to fluid conduits and removably mountable adjacent the pump. As embodied herein, and as shown in FIG. 6, cassette 104 includes an approximately Y-shaped frame 106 having a central leg portion 108, first and second arm portions 110 and 112, and a notched region 114 between the first and second arm portions. Frame 106 is preferably rigid and is mountable on chassis 12 so that central leg 108 lies adjacent the plungers 22, 24, 26 and a chassis protrusion 116 (FIG. 1) extends through notched region 114 (FIG. 6). Frame 106 may also include a lip 118 in notched region 114 for engaging with a groove (not shown) at the base of protrusion 116 to further prevent relative movement between frame 106 and chassis 12.

The Y-shape of cassette 104 together with protrusion 116 readily suggests to the operator the proper orientation of cassette 104, eliminating the possibility of wasted time during set-up.

As shown in FIG. 6, frame 106 also includes a main conduit 120 extending diagonally from central leg 108 to first arm portion 110. Main conduit 120 includes a loop port 122 near first arm portion 110 for connection with an end of main line 136. First, second, and third ports 124, 126, and 128 are located in the central leg 108 and flow connect fluid conduits such as PVC tubing segments 130, 132, 134, respectively, to main conduit 120. These ports also act to hold the respective conduits in the proper channel over the appropriate plunger when cassette 104 is attached to chassis 12 and protrusion 116 extends through notched region 114.

The cassette also supports and maintains a portion of main line 136 in a flexible tubing loop 138 for engaging peristaltic pump 90. As shown in FIG. 6, one end of tubing loop 138 is connected to loop port 122 and is held by first arm portion 110 while another end of tubing loop 138 is held by second arm portion 112. There are several ways in which first and second arm portions hold support tubing loop 138. For example, the tubing loop may be supported in part by a U-shaped groove formed in the arm portions, the tubing further clamped to the arm portions with tape or other clamping means.

Preferably, a single tubing segment connects loop port 122 to stator port 101 of centrifuge bowl 98. In this efficient manner a single piece of tubing communicates with each tubing segment 130, 132, and 134, forms loop 138, and joins cassette 104 to centrifuge bowl 98.

To facilitate disengagement of tubing loop 138 with peristaltic pump 90, a plunger solenoid 95, as shown in FIG. 1, may be mounted in chassis 12 adjacent the pump. The solenoid, upon actuation, engages tubing loop 138 to thereby eject it from the pump.

The chassis 12 may also include an air detector 140 (schematically shown in FIG. 7) protruding therefrom to detect a pressure of air in main line 136. Since the tubing must contact or be in close proximity to air detector 140 in order to accurately detect the pressure of air, frame 106 includes a cut-out portion 142 in second arm portion 112 over which a tubing segment of main line 136 passes and beneath which air detector 140 protrudes from chassis 12. As a result, an operator can push the tubing segment through the cut-out portion 142 and against the air detector 140 in order to achieve accurate air detection.

In practice, and as illustrated in FIG. 7, centrifuge bowl 98, cassette 104, fluid conduits 130, 132, and 134, and main line 136 are preferably preassembled prior to attachment to blood salvage apparatus 10. To attach the cassette and conduit lines to blood salvage apparatus 10, an operator mounts cassette 104 to chassis 12 by engaging notched region 114 with protrusion 116. Frame 106 ensures that tubing loop 138 will engage peristaltic pump 90, fluid conduit 130 will be positioned over plunger 22, fluid conduit 132 will be positioned over plunger 24, and fluid conduit 134 will be positioned over plunger 26. Channels 23, 25, and 27 in guide 30 ensure that each conduit is maintained over the proper plunger. In one quick motion using one hand, and without any risk of error, an operator can properly position each conduit on its proper plunger and simultaneously position tubing loop 138 in peristaltic pump 90. In one additional movement, valve cap 34 is pivoted and locked into place with cap lock 36 securing each conduit against the proper plunger.

The operator may then connect fluid conduit 130 to salvaged blood reservoir 150, fluid conduit 132 to saline bag 154, fluid conduit 134 to transfer bag 156, and main line 136 to a first stator port 101 of centrifuge bowl 98. A second stator port 103 of centrifuge bowl is attached to waste bag 152 via a tubing line. Alternatively, some of the fluid conduits may be preattached to their respective components. For example, main line 136 may be preattached to first stator port 101 of centrifuge bowl 98, with waste bag 152 preattached to second stator port 103 via the tubing line.

In operation, as illustrated in FIG. 7, blood is suctioned from a patient with suction wand 160 when vacuum is applied to blood reservoir 150 via vacuum pump 162. At this time, each of the plungers may be in the extended or closed positioned to prevent blood or other fluids from flowing directly into centrifuge bowl 98. Anticoagulant from anticoagulant bag 164 may be added to the suction line to prevent clotting.

To fill the centrifuge bowl with blood, an operator manipulates control panel 14 to activate pump 90, retract plunger 22, and thereby allow blood to flow from reservoir 150 to centrifuge bowl 98. When the centrifuge bowl is filled, plunger 22 is extended to prevent further blood from flowing into centrifuge bowl 98. Centrifuge 96 turns bowl 98 to separate the red blood cells from the plasma and waste products of the received blood a s described, for example, in U.S. Pat. No. 5,141,486. The red blood cells are retained in centrifuge bowl 98 while the plasma and waste is sent, by centrifugal force, out of second stator port 103 and into waste bag 152.

When the centrifuge operation is completed, the operator can activate a "wash" cycle by manipulating control panel 14, which retracts plunger 24 and activates peristaltic pump 90 so that saline flows into centrifuge bowl 98. Centrifuge 96 is activated and plunger 24 is then closed after a sufficient amount of saline enters centrifuge bowl 98 to wash the red blood cells with the saline and separate any remaining impurities from the red blood cells. The impurities and added saline flow into waste bag 152.

If no further washing is desired, the operator can transfer the "washed" red blood cells to transfer bag 156 by manipulating control panel 14, which reverses peristaltic pump 90 and retracts plunger 26 so that the red blood cells flow into transfer bag 156 for later reinfusion into the patient. After use, centrifuge bowl 98, cassette 104, and the conduits may be discarded and replaced.

The blood salvage operation described above may also be accomplished automatically rather than manually, in accordance with a predetermined program. With automatic operation, an optical sensor (not shown) detects the volume of packed red blood cells in the centrifuge bowl and alters the operation at preset volumetric transition points.

It will be apparent to those skilled in the art that various modifications and variations can be made in the system of the present invention without departing from the scope or spirit of the invention. Thus, it is intended that the present invention cover the modifications and variations of this invention provided they come within the scope of the claims and their equivalents.

What is claimed is:

1. A blood salvage assembly mountable on a chassis having a peristaltic pump and first, second, and third plungers located thereon and a chassis protrusion protruding therefrom, the assembly comprising:

an approximately Y-shaped frame having a central leg portion, first and second arm portions, and a notched region between the first and second arm portions, the frame being configured to be selectively mountable on the chassis so that the central leg lies adjacent the plungers and the chassis protrusion extends through the notched region;

a main conduit connected to the frame and extending from the leg portion toward the first arm portion, the main conduit having a loop port in an area of the first arm portion;

a first tubing segment;

second tubing segment;

a third tubing segment;

a first port in the frame, the first port connecting the first tubing segment to the main conduit, and being configured to hold the first tubing segment over the first plunger when the frame is mounted on the chassis and the protrusion extends through the notched region;

a second port in the frame, the second port connecting the second tubing segment to the main conduit, and being configured to hold the second tubing segment over the second plunger when the frame is mounted on the chassis and the protrusion extends through the notched region;

a third port in the frame, the third port connecting the third tubing segment to the main conduit, and being configured to hold the third tubing segment over the third plunger when the frame is mounted on the chassis and the protrusion extends through the notched region;

a centrifuge bowl having a stator, the stator having a first port and a second port; and a fourth tubing segment having a first end connected to the loop port and a second end connected to the first centrifuge bowl stator port, the fourth tubing segment being secured at an intermediate portion thereof to the second arm thereby forming a loop between the first and second arms for engaging the peristaltic pump when the protrusion extends through the notched region.

2. A blood salvage assembly as set forth in claim 1, wherein the frame includes a cut-out portion over which a portion of the fourth tubing segment passes and beneath which an air detector protrudes when the frame is mounted on the chassis.

3. A blood salvage assembly as set forth in claim 1, further comprising a fluid container and a fifth tubing segment connecting the second centrifuge bowl stator port to the fluid container.

4. A fluid cassette and tubing combination for connection to first, second, and third tubes, and mountable on a chassis having a peristaltic pump and a series of plungers located thereon and a chassis protrusion protruding therefrom, the cassette and tubing combination comprising:

an approximately Y-shaped frame having a central leg portion, first and second arm portions, and a notched region between the first and second arm portions, the frame being configured to be selectively mountable on the chassis so that when the frame is mounted on the chassis the central leg lies adjacent the plungers and the chassis protrusion extends through the notched region;

a main conduit located on the frame and extending from the leg portion toward the first arm portion, the main conduit having a loop port in an area of the first arm portion;

a first port in the frame, the first port being configured to connect the first tube to the main conduit, and to hold the first tube over a first plunger when the frame is mounted on the chassis and the protrusion extends through the notched region;

a second port in the frame, the second port being configured to connect the second tube to the main conduit, and to hold the second tube over a second plunger when the frame is mounted on the chassis and the protrusion extends through the notched region;

a third port in the frame the third port being configured to connect the third tube to the main conduit, and to hold the third tube over a third plunger when the frame is mounted on the chassis and the protrusion extends through the notched region; and a flexible tubing loop for engaging the peristaltic pump when the frame is mounted on the chassis and the protrusion extends through the notched region, the tubing loop having a first end connected to the loop port and a second end secured to the second arm of the frame.

5. A cassette and tubing combination as set forth in claim 4, wherein the frame includes a cut-out portion over which a tubing segment passes and beneath which an air detector protrudes when the frame is mounted on the chassis.

6. An assembly including a fluid cassette, the assembly comprising:

a frame defining the fluid cassette, the frame having an approximately Y-shaped configuration including a pair of legs and a central portion extending from a location at an intersection of the legs;

a first port connected to the frame;

a second port connected to the frame;

a third port connected to the frame;

a main conduit connected to the frame such that the first port, the second port, and the third port are flow connected to the main conduit; and a tubing loop connected to the frame at at least two locations, the tubing loop being flow connected to the main conduit.

7. An assembly as set forth in claim 6 wherein the first, second, and third ports are arranged in side-by-side relation in order to hold tubing segments in side-by-side channels of a tubing occlusion device.

8. An assembly as set forth in claim 6 wherein the frame includes a cut-out portion over which a tubing segment extends, the cut-out portion being configured to overlay a detector when the frame is mounted on a chassis.

9. An assembly as set forth in claim 6 further including a first channel connecting the first port to the main conduit, a second channel connecting the second port to the main conduit, and a third channel connecting the third port to the main conduit, wherein each of the first port, the second port, the third port, the first channel, the second channel, the third channel, the fourth channel, and the main conduit are integrally formed with the frame.

10. An assembly as set forth in claim 6 further including a centrifuge bowl having a stator with a first stator port and a second stator port, the first stator port being flow-connected to the tubing loop.

11. An assembly as set forth in claim 10 further including a reservoir flow-connected with the second stator port.

12. An assembly as set forth in claim 6 further including a notched region between the legs for engaging a protrusion on a machine on which the cassette is used.

13. An assembly as set forth in claim 9 wherein the first channel, the second channel, and the third channel have rigid walls and the tubing loop has flexible walls.

* * * * *